US007795786B2

(12) United States Patent
Nakayama et al.

(10) Patent No.: US 7,795,786 B2
(45) Date of Patent: Sep. 14, 2010

(54) ULTRASONIC PROBE AND METHOD OF MANUFACTURING THE SAME

(75) Inventors: Ryuichi Nakayama, Ashigarakami-gun (JP); Atsushi Osawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/401,968

(22) Filed: Mar. 11, 2009

(65) Prior Publication Data

US 2009/0236940 A1 Sep. 24, 2009

(30) Foreign Application Priority Data

Mar. 21, 2008 (JP) ............................. 2008-073772
Nov. 28, 2008 (JP) ............................. 2008-304103

(51) Int. Cl.
*H01L 41/047* (2006.01)
*H01L 41/083* (2006.01)

(52) U.S. Cl. ...................... 310/334; 310/366

(58) Field of Classification Search ................. 310/334, 310/366

See application file for complete search history.

(56) References Cited

U.S. PATENT DOCUMENTS 6,437,487 B1 * 8/2002 Mohr et al. ................. 310/365
7,148,607 B2 * 12/2006 Sato ........................... 310/334
7,316,059 B2 * 1/2008 Sato ........................... 29/594

FOREIGN PATENT DOCUMENTS

JP  2000-117973 A  4/2000
JP  2006-320512 A  11/2006

* cited by examiner

*Primary Examiner*—Thomas M Dougherty
(74) *Attorney, Agent, or Firm*—Sughrue Mion, PLLC

(57) ABSTRACT

In an ultrasonic probe in which individual wires led out from multilayered piezoelectric elements are arranged in a staggered manner, short-circuit is prevented. Each of the elements includes: a multilayered structure in which piezoelectric material layers and at least one internal electrode are stacked; first and second flat electrodes; first and second side electrodes; an insulating film formed at a second side surface side of the multilayered structure; a wiring member bonded to the first flat electrode on the one end of the multilayered structure by using a conducting adhesive material; and the wiring member is provided at the second side surface side of the multilayered structure and the insulating film electrically separates the second side electrode and the conducting adhesive material in a first element, and the wiring member is provided at a first side surface side of the multilayered structure in a second element.

6 Claims, 9 Drawing Sheets

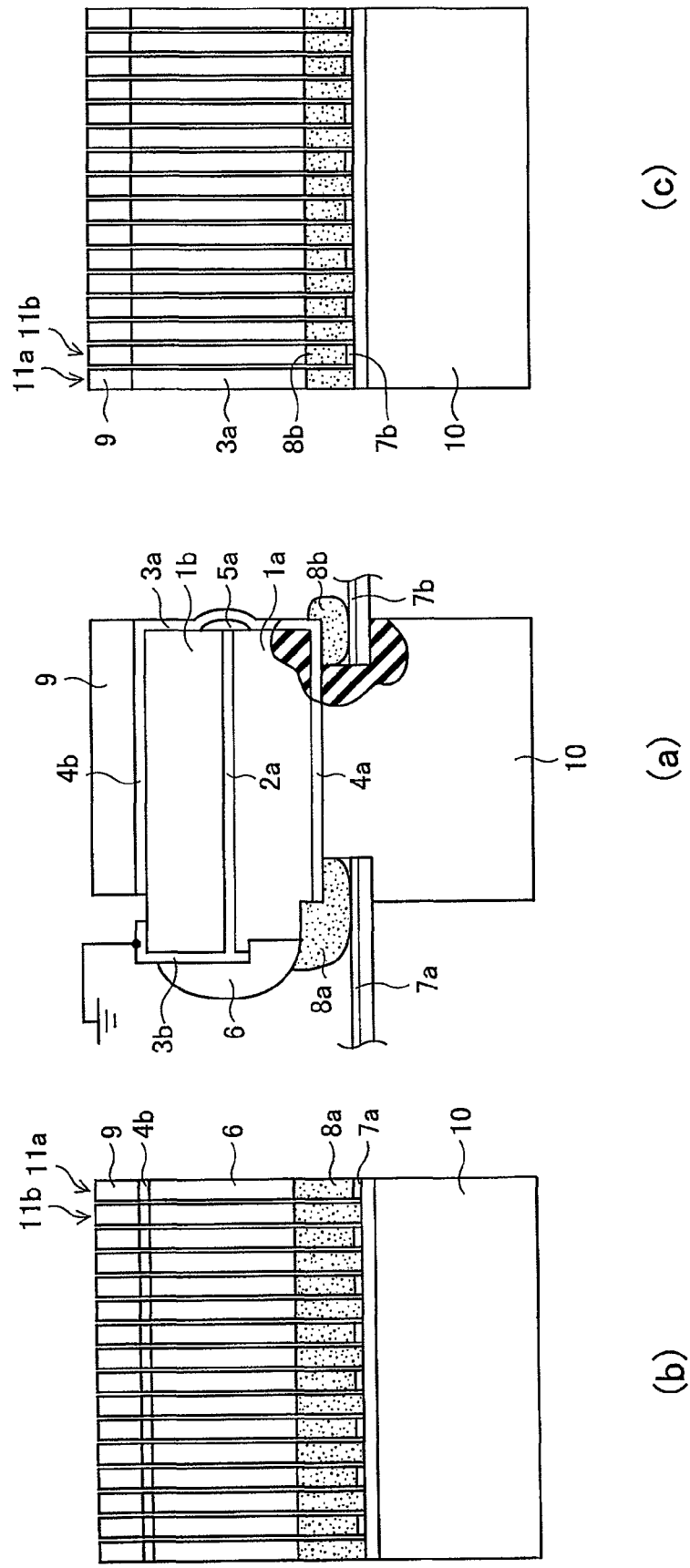

ULTRASONIC PROBE AND METHOD OF MANUFACTURING THE SAME

BACKGROUND OF THE INVENTION

1. Field of the Invention

The present invention relates to an ultrasonic probe including plural ultrasonic transducers for transmitting and/or receiving ultrasonic waves in an ultrasonic diagnostic apparatus for medical use or structure flaw detection, and a method of manufacturing such an ultrasonic probe.

2. Description of a Related Art

In medical fields, various imaging technologies have been developed in order to observe the interior of an object to be inspected and make diagnoses. Especially, ultrasonic imaging for acquiring interior information of the object by transmitting and receiving ultrasonic waves enables image observation in real time without exposure to radiation like other medical image technologies such as X-ray photography or RI (radio isotope) scintillation camera. Accordingly, ultrasonic imaging is utilized as an imaging technology at a high level of safety in a wide range of departments including not only the fetal diagnosis in the obstetrics, but also gynecology, circulatory system, digestive system, and so on.

The ultrasonic imaging is an image generation technology utilizing the nature of ultrasonic waves that the waves are reflected at a boundary between regions with different acoustic impedances (e.g., a boundary between structures). Typically, an ultrasonic diagnostic apparatus (or referred to as an ultrasonic imaging apparatus or an ultrasonic observation apparatus) is provided with an ultrasonic probe to be used in contact with the object or ultrasonic probe to be used by being inserted into a body cavity of the object. Alternatively, an ultrasonic endoscope of an endoscope for optically observing the interior of the object in combination with an ultrasonic probe for intracavity is also used.

In the ultrasonic probe, for example, a piezoelectric vibrator (piezoelectric element) having electrodes formed on both ends of a piezoelectric material is used as an ultrasonic transducer for transmitting and/or receiving ultrasonic waves. When a voltage is applied to the electrodes of the vibrator, the piezoelectric material expands and contracts to generate ultrasonic waves. Further, plural vibrators are one-dimensionally or two-dimensionally arranged and the vibrators are sequentially driven by drive signals provided with predetermined delays, and thereby, an ultrasonic beam can be formed toward a desired direction. On the other hand, the vibrator receives the propagating ultrasonic waves, expands and contracts, and generates an electric signal. The electric signal is used as a reception signal of ultrasonic waves.

In an array type ultrasonic probe as described above, a common electrode (ground electrode) and individual electrodes (address electrodes) are provided for the respective elements. In order to lead out wires from the individual electrodes of the respective elements, at least one substrate for wiring is bonded to the electrodes formed on the upper or lower surface of the piezoelectric materials by using a conducting adhesive material.

The structure of a piezoelectric element is basically a single-layer structure in which electrodes are formed on both ends of one piezoelectric material. However, according to microfabrication and integration of piezoelectric elements with recent developments of MEMS (micro electro mechanical systems) related devices, multilayered piezoelectric elements each having plural piezoelectric materials and plural electrodes alternately stacked have been used. In such a piezoelectric element, the capacitance of the multilayered structure as a whole can be made larger by connecting electrodes for applying electric fields to the respective plural piezoelectric material layers in parallel. Accordingly, the rise in electrical impedance can be suppressed even when the size of the piezoelectric element is made smaller.

The multilayered piezoelectric elements used in the ultrasonic probe are roughly classified into (i) elements having internal electrodes with a whole-surface electrode structure and (ii) elements internal electrodes with an alternating electrode structure. In either structure, the internal electrodes are alternately connected to the common electrode and the individual electrodes respectively formed on the upper and lower surfaces of the multilayered piezoelectric element via side electrodes so as to apply electric fields to the piezoelectric materials in the respective layers.

By the way, as the probe is made smaller, the widths of the vibrators included in the array become smaller, the wiring pattern widths on the substrate for individual wiring become narrower, and the spacings between adjacent wiring patterns become narrower, and thus, the work for leading out the individual wires becomes difficult. In order to solve the problem, a technique of connecting the substrate for individual wiring to the piezoelectric elements such that the individual wires are led out from not only one side along the longitudinal direction of the piezoelectric elements but both sides along the longitudinal direction at twice pitch to be arranged in a staggered manner. In the case where the individual wires are led out in such a manner, the individual wires are divided into odd number channels and even number channels at both sides along the longitudinal direction of the piezoelectric elements. Hereinafter, a manner according which the individual wires are led out as described above is called "staggered manner" for convenience. According to the technique, the lead-out parts of the individual wires are alternately formed on both sides of the piezoelectric materials, and the spacings between adjacent electrodes become wider and the workability is improved. However, at the same time, another substrate for individual wiring is bonded on the same side of the common electrode and, if the conducting adhesive flows out when the other substrate for individual wiring is bonded, it is highly likely that the conducting adhesive is short-circuited to the side electrodes of the multilayered piezoelectric element.

In the case of an ultrasonic probe using single-layered piezoelectric elements, especially, the distance between electrodes becomes smaller as the piezoelectric material becomes thinner for higher frequency. If the conducting adhesive is spread out for bonding the substrates for individual wiring, it easily runs along the side surfaces of the piezoelectric materials and causes short-circuit. For example, when the distance between electrodes is 130 μm, the yield is 50%. In the case of using the multilayered piezoelectric elements, the electrodes are also on the side surfaces of the piezoelectric elements and the distance between electrodes becomes extremely small. If the conducting adhesive flows out when the substrates for individual wiring are bonded, the conducting adhesive easily contacts the side electrodes and causes short-circuit.

As a related technology, Japanese Patent Application Publication JP-P2000-117973A discloses a piezoelectric vibrator unit in which even when the widths of piezoelectric vibrators are made narrower, the continuity between the electrodes at the piezoelectric vibrator side and the conducting pattern of flexible tapes is reliably secured and short-circuit due to excessive solder is not caused. The piezoelectric vibrator unit is configured such that the effective continuity widths of the conducting pattern in the connecting part of the flexible tapes are provided wider than the widths of the piezoelectric vibrators and a non-superposing area that does not superpose on the conducting patterns in the connecting part of the piezoelectric vibrators is provided, and thereby, the excessive solder melted at bonding of the conducting patterns is escaped to the non-superposing area.

Further, Japanese Patent Application Publication JP-P2006-320512A discloses an ultrasonic vibrator that provides increased acoustic output by multilayered connection of plural electromechanical conversion elements with connecting members. The ultrasonic vibrator includes electromechanical conversion elements that convert electric signals into mechanical operation to radiate ultrasonic waves, an acoustic matching layer material provided at the ultrasonic radiation surface side of the electromechanical conversion elements, a backing material provided on the opposite surface to the ultrasonic radiation surface side of the electromechanical conversion elements, a connecting member plastically deformed for electric connection to the electromechanical conversion elements, and an insulating member provided on the surface of the connecting member other than the part that is electrically connected.

However, JP-P2000-117973A and JP-P2006-320512A do not disclose prevention of short-circuit to the side electrodes of the multilayered piezoelectric element caused by the conducting adhesive flowing out when individual wires are bonded in the case where the individual wires lead out from the multilayered piezoelectric elements are arranged in a staggered manner.

SUMMARY OF THE INVENTION

The present invention has been achieved in view of the above-mentioned problems. A purpose of the present invention is, in an ultrasonic probe including plural multilayered piezoelectric elements, in the case where individual wires led out from the multilayered piezoelectric elements are arranged in a staggered manner, to prevent short-circuit to side electrodes of the multilayered piezoelectric elements caused if a conducting adhesive flows out when the individual wires are bonded. A further purpose of the present invention is to improve mechanical strength of the side electrodes.

In order to accomplish the purposes, an ultrasonic probe according to one aspect of the present invention is an ultrasonic probe including plural multilayered piezoelectric elements arranged in a row, and each of the plural multilayered piezoelectric elements includes: a multilayered structure in which plural piezoelectric material layers and at least one internal electrode are alternately stacked; a first flat electrode formed on a piezoelectric material layer located on one end of the multilayered structure; a second flat electrode formed on a piezoelectric material layer located on the other end of the multilayered structure; a first side electrode formed on a first side surface of the multilayered structure and connected to odd-numbered electrodes of the first and second flat electrodes and the at least one internal electrode, the odd-numbered electrodes including the first flat electrode; a second side electrode formed on a second side surface of the multilayered structure and connected to even-numbered electrodes of the first and second flat electrodes and the at least one internal electrode; an insulating film formed at a second side surface side of the multilayered structure; a wiring member bonded to the first flat electrode on the one end of the multilayered structure by using a conducting adhesive material; wherein the wiring member is provided at the second side surface side of the multilayered structure in a first multilayered piezoelectric element of the plural multilayered piezoelectric elements, the wiring member is provided at a first side surface side of the multilayered structure in a second multilayered piezoelectric element adjacent to the first multilayered piezoelectric element of the plural multilayered piezoelectric elements, and the insulating film electrically separates the second side electrode and the conducting adhesive material in the first multilayered piezoelectric element.

Further, a method of manufacturing an ultrasonic probe according to one aspect of the present invention is a method of manufacturing an ultrasonic probe including plural multilayered piezoelectric elements arranged in a row, and the method includes the steps of: (a) fabricating a multilayered structure in which plural piezoelectric material layers and at least one internal electrode are alternately stacked; (b) applying a coating around the multilayered structure with a conducting film and removing parts of the conducting film to form a first flat electrode formed on a piezoelectric material layer located on one end of the multilayered structure, a second flat electrode formed on a piezoelectric material layer located on the other end of the multilayered structure, a first side electrode formed on a first side surface of the multilayered structure and connected to odd-numbered electrodes of the first and second flat electrodes and the at least one internal electrode, the odd-numbered electrodes including the first flat electrode, and a second side electrode formed on a second side surface of the multilayered structure and connected to even-numbered electrodes of the first and second flat electrodes and the at least one internal electrode; (c) forming an insulating film at a second side surface side of the multilayered structure; (d) bonding a wiring member to the first flat electrode on the one end of the multilayered structure by using a conducting adhesive material; and (e) cutting the multilayered structure to manufacture the plural multilayered piezoelectric elements; wherein the wiring member is provided at the second side surface side of the multilayered structure in a first multilayered piezoelectric element of the plural multilayered piezoelectric elements, the wiring member is provided at a first side surface side of the multilayered structure in a second multilayered piezoelectric element adjacent to the first multilayered piezoelectric element of the plural multilayered piezoelectric elements, and the insulating film electrically separates the second side electrode and the conducting adhesive material in the first multilayered piezoelectric element.

According to one aspect of the present invention, since the insulating film electrically separates the second side electrode and the conducting adhesive material in the first multilayered piezoelectric element, the short-circuit to side electrodes of the multilayered piezoelectric elements caused if the conducting adhesive flows out when the individual wires are bonded can be prevented. As a result, the difficulty level of working at manufacturing can be reduced and the yield can be improved. Further, the side electrodes are physically weak, but the resistance to the mechanical damage in manufacturing can be provided when the side electrodes are covered by the insulating film.

BRIEF DESCRIPTION OF THE DRAWINGS

FIG. 7 shows an internal structure of an ultrasonic probe according to the sixth embodiment of the present invention.

DESCRIPTION OF THE PREFERRED EMBODIMENTS

Figure 1:
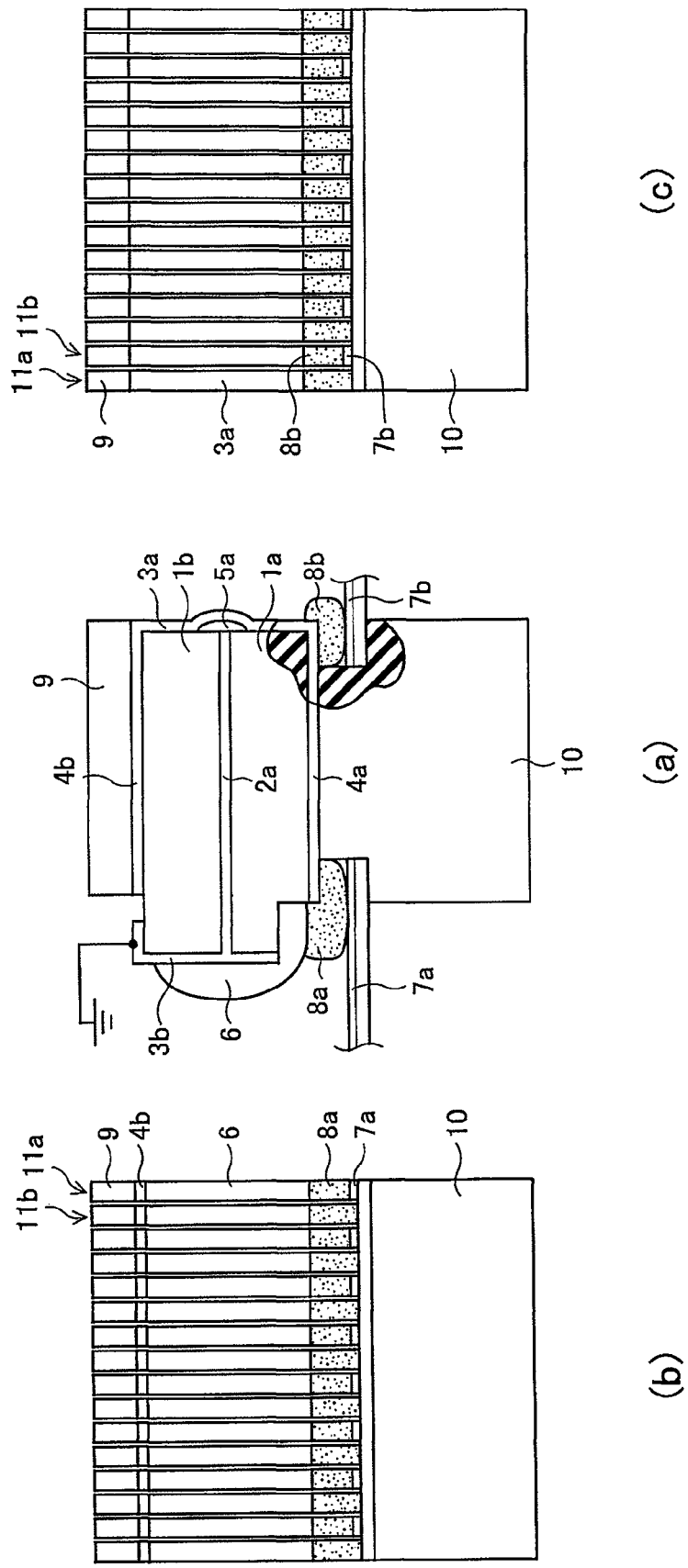
FIG. 1 shows an internal structure of an ultrasonic probe according to the first embodiment of the present invention.

Hereinafter, preferred embodiments of the present invention will be explained in detail with reference to the drawings. The same reference numerals will be assigned to the same component elements and the description thereof will be omitted.

FIG. 1 shows an internal structure of an ultrasonic probe according to the first embodiment of the present invention. In FIG. 1, (a) is a front view, (b) is a left-side view, and (c) is a right-side view.

The ultrasonic probe includes plural multilayered piezoelectric elements 11a and 11b arranged in a row. Each of the multilayered piezoelectric elements has a multilayered structure in which plural piezoelectric layers 1a and 1b and at least one internal electrode 2a are alternately stacked, a flat electrode 4a formed on the piezoelectric layer 1a located at the lower end of the multilayered structure, a flat electrode 4b formed on the piezoelectric layer 1b located at the upper end of the multilayered structure, an insulating film 5a formed on the right side surface of the multilayered structure, a side electrode 3a formed on the right side surface of the multilayered structure and connected to odd-numbered electrodes of the flat electrodes 4a and 4b and the at least one internal electrode 2a, in which the odd-numbered electrodes includes the flat electrode 4a, a side electrode 3b formed on the left side surface of the multilayered structure and connected to even-numbered electrodes of the flat electrodes 4a and 4b and the at least one internal electrode 2a, an insulating film 6 formed on the left side surface of the multilayered structure, and a wiring member 7a or 7b connected to the flat electrode 4a using a conducting adhesive material 8a or 8b at the lower end of the multilayered structure.

The two kinds of multilayered piezoelectric elements 11a and 11b are one-dimensionally and alternately arranged and supported by a backing material 10. An acoustic matching layer 9 for providing acoustic matching to reduce the reflection of ultrasonic waves at the boundary of an object to be inspected is provided on the multilayered piezoelectric elements 11a and 11b.

Here, the flat electrode 4a, the side electrode 3a, and the main part of the flat electrode 4b correspond to individual electrodes, and the side electrode 3b and a part of the flat electrode 4b correspond to the common electrode. Generally, the common electrode is connected to the ground potential. As the wiring member 7a or 7b, for example, plural wiring patterns for individual wiring formed on a flexible substrate is used. To arrange the lead wires of the individual electrodes from the multilayered piezoelectric elements in a staggered manner, the wiring member 7a is provided at the left side surface side of the multilayered structure in the multilayered piezoelectric element 11a, and the wiring member 7b is provided at the right side surface side of the multilayered structure in the multilayered piezoelectric element 11b.

In the embodiment, in the multilayered piezoelectric element 11a, the insulating film 6 electrically isolates the side electrode 3b and the conducting adhesive material 8a, and thereby, the short-circuit caused between them is prevented and the mechanical strength of the side electrode 3b is improved. In the example shown in FIG. 1, the insulating film 6 covers nearly the entire exposed surfaces of the side electrode 3b.

The piezoelectric material layers 1a and 1b are formed by using a piezoelectric material of PZT (Pb(lead) zirconate titanate) or the like, and have thicknesses of about 130 μm or less, for example. Further, the internal electrode 2a is formed by using a metal material of platinum (Pt), silver palladium (Ag—Pd), or the like, and has a thickness of 1 μm to 3 μm, for example.

As the side electrodes 3a and 3b and the flat electrodes 4a and 4b, for example, electrodes of one kind of material selected from gold (Au), platinum (Pt), titanium (Ti), or the like, two-layer structure electrodes of chromium (Cr) and gold (Au), or three-layer structure electrodes of nickel (Ni), titanium (Ti), and platinum (Pt) are used.

As the insulating films 5a and 6, for example, a highly insulating resin including a thermoplastic resin such as an epoxy or silicone resin and a light curing resin such as urethane acrylate or oxetane resin, for example. In such a resin, the Young's modulus is $1.3 \times 10^9$ Pa to $2.0 \times 10^9$ Pa, which is much smaller than that of glass or the like. Accordingly, when the piezoelectric material layers 1a and 1b are expanding and contracting, the insulating films 5a and 6 can follow the expansion and contraction (deformation) of the piezoelectric material layers 1a and 1b, and thus, there is little braking of the deformation of the piezoelectric material layers 1a and 1b due to the insulating films 5a and 6.

FIGS. 2A-2G are diagrams for explanation of a method of manufacturing the ultrasonic probe according to the first embodiment of the present invention. Here, the case where an ultrasonic probe including multilayered piezoelectric elements having two piezoelectric material layers is manufactured will be explained.

Figure 2A:
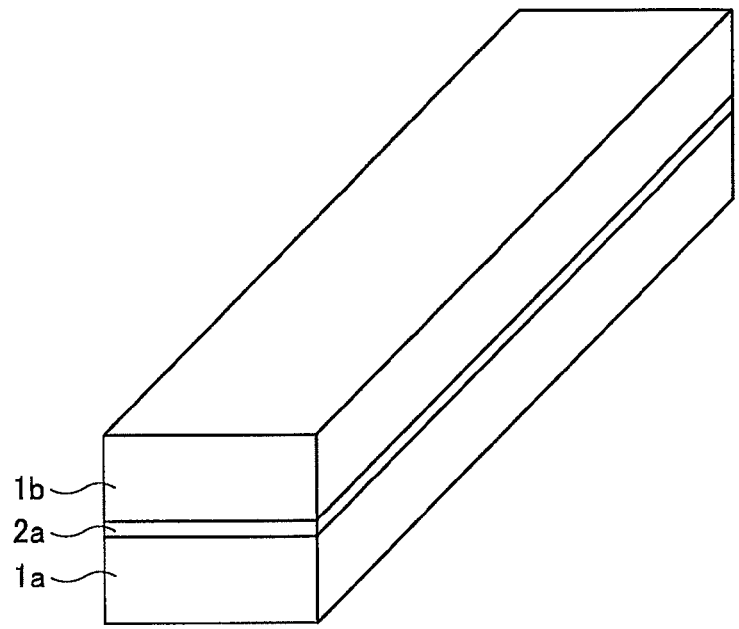
FIGS. 2A-2G are diagrams for explanation of a method of manufacturing the ultrasonic probe according to the first embodiment of the present invention.

First, as shown in FIG. 2A, a multilayered structure is fabricated by stacking the piezoelectric material layer 1a, the internal electrode 2a, and the piezoelectric material layer 1b. The multilayered structure may be fabricated, for example, using the green sheet method, by stacking piezoelectric bulk materials having internal electrode formed therein, or using the aerosol deposition (AD) method of depositing a powdery material by spraying the material toward the lower layer at a high speed. The AD method is a film forming method that has recently attracted attention as a method of forming a ceramics film.

Figure 2B:
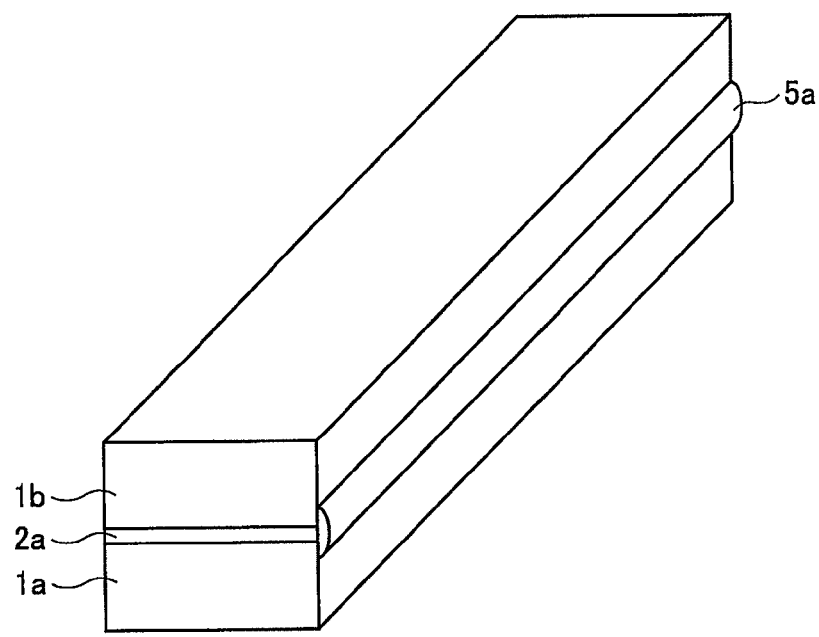

Then, as shown in FIG. 2B, the insulating film 5a for covering the end of the internal electrode 2a is formed on one side surface (on the right side in the drawing) of the multilayered structure. Here, the step of forming the insulating film can be made easier using a light curing resin. Further, a liquid-state light curing resin can be provided in a predetermined region of the multilayered structure using a dispenser.

Figure 2C:
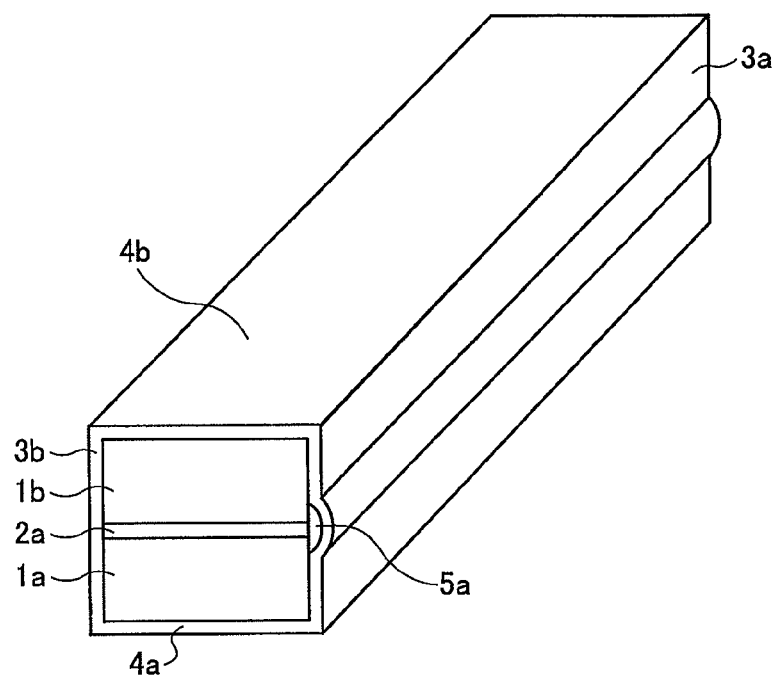

Then, as shown in FIG. 2C, the multilayered structure is coated with electrode materials (conducting films) to be the side electrodes 3a and 3b and the flat electrodes 4a and 4b by physical deposition method such as sputtering, for example. The formation of the electrode materials may be performed continuously or separately with respect to the two side surfaces and the two flat surfaces. Further, the formation of the electrode materials is avoided on the front surface and the rear surface of the multilayered structure.

Figure 2D:
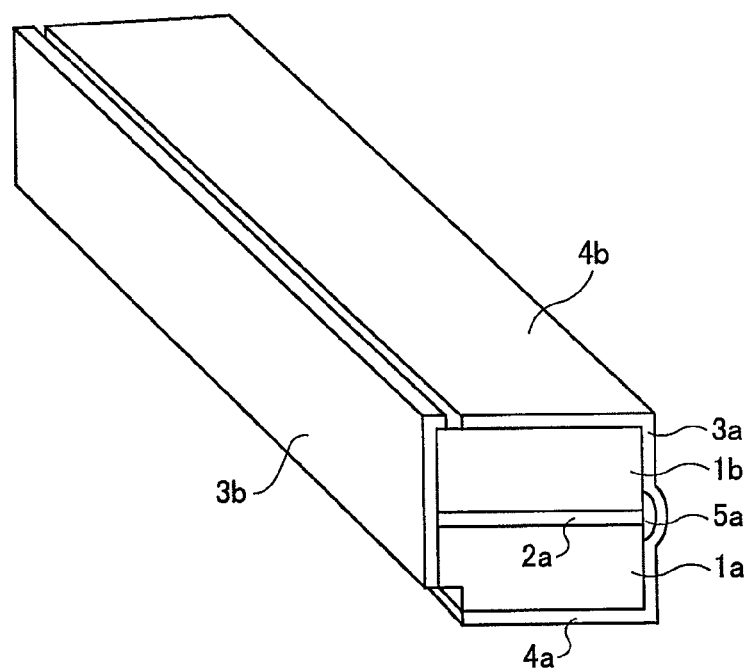

Then, as shown in FIG. 2D, in order to electrically divide the flat electrode 4a and the side electrode 3b, a groove is formed in the corner part of the multilayered structure (including a part of the piezoelectric material layer 1a) where the surface including the flat electrode 4a and the surface including the side electrode 3b intersect. In this example, using a dicing blade attached to a dicing saw or cutting saw and rotated, the corner part of the multilayered structure is cut off in the array arrangement direction. Further, in order to electrically divide the flat electrode 4a and the side electrode 3b, another groove is formed in the flat electrode 4b. In this example, using the dicing blade, the electrode material of the flat electrode 4b near the end at the side electrode 3b is cut off in the array arrangement direction.

Figure 2E:
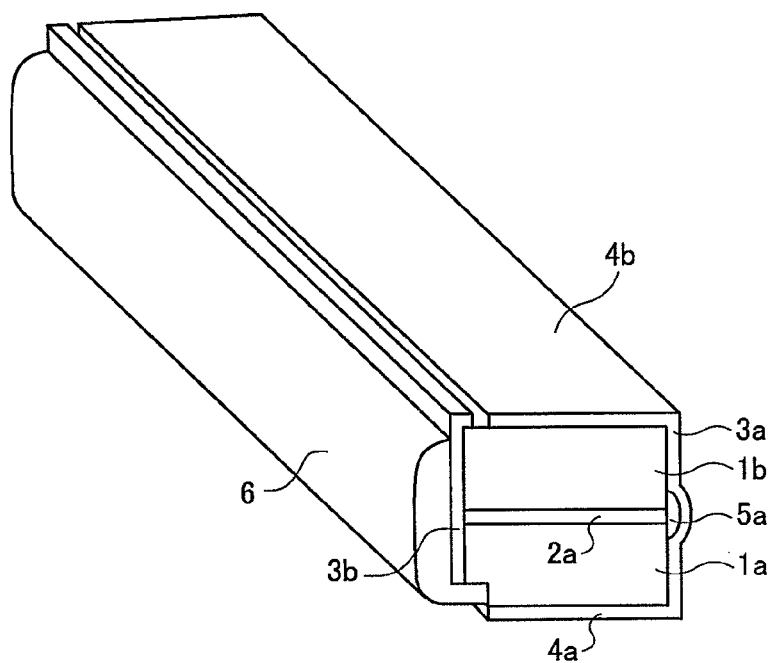

Then, as shown in FIG. 2E, the insulating film 6 is formed by applying a highly insulating resin to the surface of the side electrode 3b and a part of the cut off part (groove) including the end of the side electrode 3b. In this example, the insulating film 6 covers nearly the entire exposed surface of the side electrode 3b, however, the insulating film 6 may cover the only the part near the end of the side electrode 3b as long as the conducting adhesive material 8a (FIG. 1) do not contact the side electrode 3b. Further, in the cut off part, the insulating film 6 covers the end of the side electrode 3b but does not cover the end of the flat electrode 4a. Here, the step of forming the insulating film can be made easier using a light curing resin. Further, a liquid-state light curing resin can be provided in a predetermined region of the multilayered structure using a dispenser.

Figure 2F:
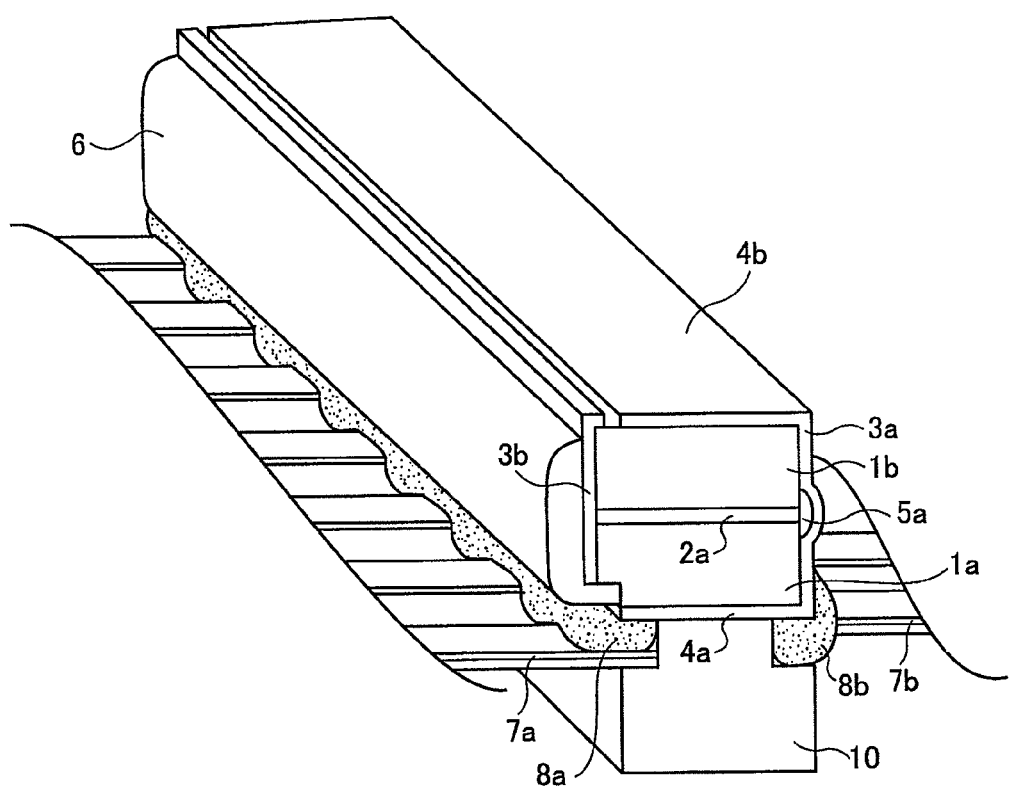

Then, as shown in FIG. 2F, under the condition that the multilayered piezoelectric element is supported by the backing material 10, the left wiring member 7a and the right wiring member 7b are provided such that the left and right wiring patterns are alternately arranged in the array arrangement direction. Then, using the conducting adhesive materials 8a and 8b, the wiring member 7a is bonded to the end of the flat electrode 4a at the side electrode 3b side and the wiring member 7b is bonded to the end of the flat electrode 4a at the side electrode 3a side. Here, the conducting adhesive material 8a is formed on the insulating film 6 as well, and electrically insulated from the side electrode 3b by the insulating film 6.

Figure 2G:
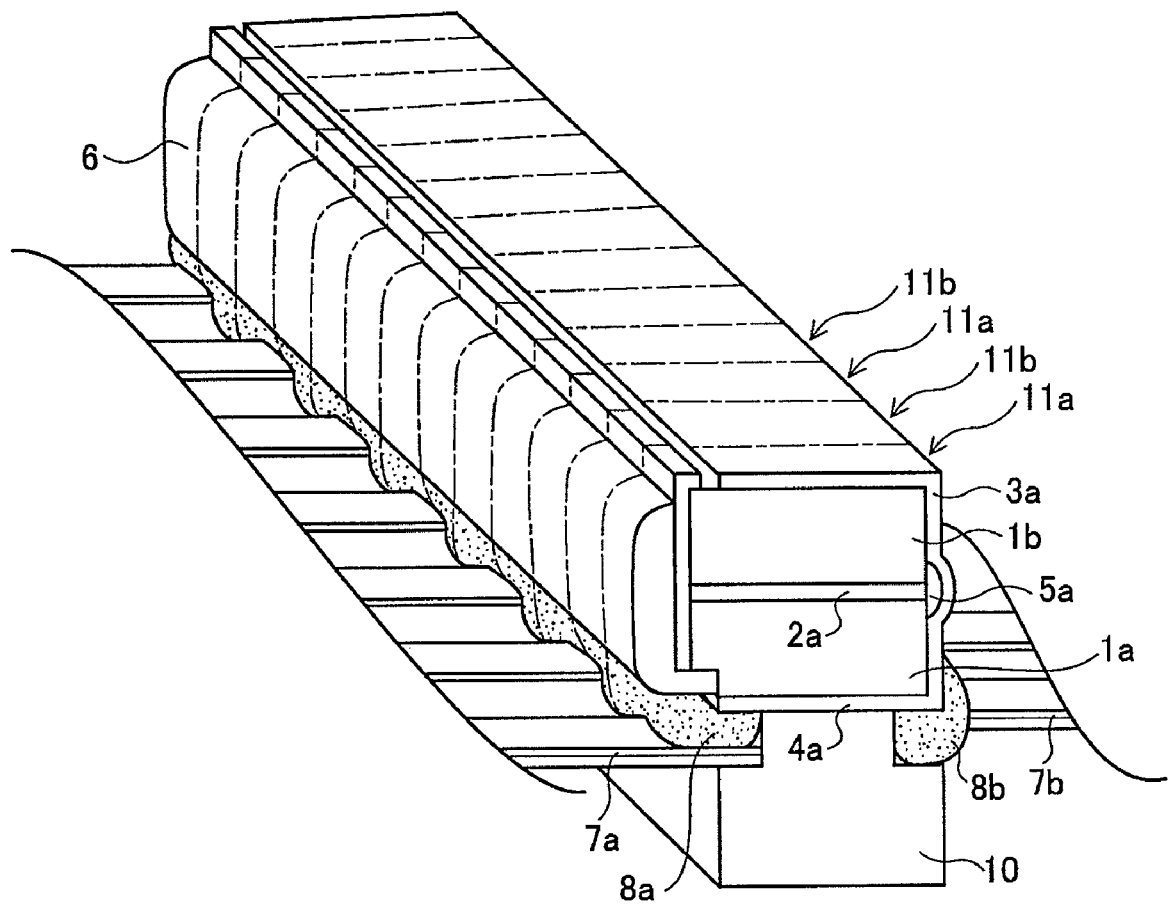

As shown in FIG. 2G, the multilayered structure on which the side electrodes 3a and 3b, the flat electrodes 4a and 4b, and the insulating films 5a and 6 have been formed is cut at predetermined distances (corresponding to the half of the arrangement pitch of the wiring members 7a or 7b), and thus, a group of one-dimensionally arranged multilayered piezoelectric elements are formed. At the same time, also the conducting adhesive material 8a and the conducting adhesive material 8b are cut and the adjacent multilayered piezoelectric elements are insulated. Thereby, array structures in which the multilayered piezoelectric element 11a and the multilayered piezoelectric element 11b are alternately stacked are completed, and those multilayered piezoelectric elements 11a and 11b function as ultrasonic transducers (piezoelectric vibrators) of the ultrasonic probe.

In the multilayered piezoelectric element, the area of opposed electrodes becomes larger than that of the single-layered vibrator, and the electric impedance becomes lower. Therefore, the multilayered piezoelectric element operates more efficiently for the applied voltage than a single-layered piezoelectric vibrator having the same size. Specifically, given that the number of piezoelectric material layers is N, the number of the piezoelectric material layers is N-times the number of that of the single-layered piezoelectric vibrator and the thickness of each piezoelectric layer is 1/N of the thickness of that of the single-layered piezoelectric vibrator, and the electric impedance of the vibrator is $1/N^2$-times that of the single-layered piezoelectric vibrator. Therefore, the electric impedance of the vibrator can be adjusted by increasing or decreasing the number of stacked piezoelectric material layers, and thus, the electric impedance matching between a drive circuit or signal cable and itself is easily provided, and the sensitivity can be improved.

Next, the second embodiment of the present invention will be explained. In the first embodiment, the example of multilayered structure of whole surface electrode structure having two piezoelectric material layers has been shown, however, in the second embodiment, an example of multilayered structure of whole surface electrode structure having three piezoelectric material layers will be shown.

Figure 3:
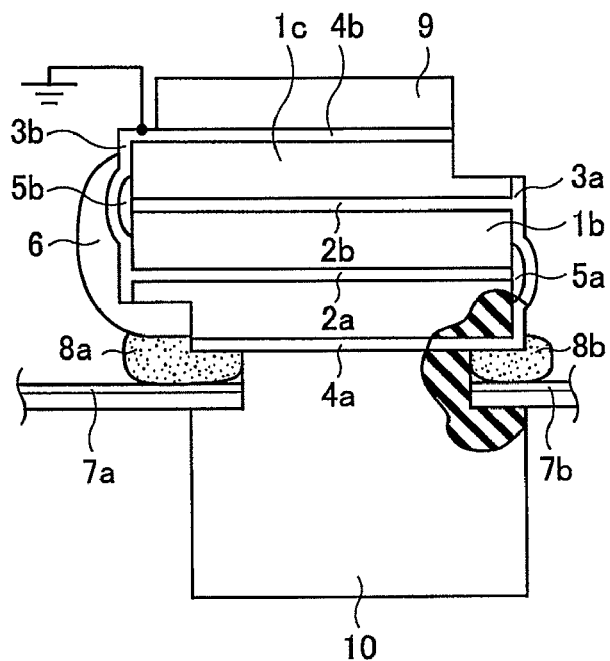
FIG. 3 is a front view showing an ultrasonic probe according to the second embodiment of the present invention.

FIG. 3 is a front view showing an ultrasonic probe according to the second embodiment of the present invention. As shown in FIG. 3, as the third piezoelectric material layer, a piezoelectric material layer 1c is provided on the piezoelectric material layer 1b via an internal electrode 2b. An insulating film 5b is formed on the end of the internal electrode 2b at the side electrode 3b side, and the internal electrode 2b is electrically connected to the side electrode 3a and electrically insulated from the side electrode 3b. Further, a notch part (groove) that cuts the side electrode 3a side in the array arrangement direction is provided in the flat electrode 4b and the piezoelectric material layer 1c. Accordingly, the flat electrode 4b is electrically connected to the side electrode 3b and electrically insulated from the side electrode 3a. Thereby, the same electric field as that for the piezoelectric material layer 1a is applied to the piezoelectric material layer 1c.

In this manner, in the case of the multilayered piezoelectric element having three or more piezoelectric material layers, the end of the internal electrode is connected to either of the side electrode 3a or 3b and the insulating film is formed on the opposite end such that the opposed two electrodes have reverse polarity to each other. Further, the flat electrode 4b is also connected to either of the side electrode 3a or 3b so as to have reverse polarity to the facing electrode. Note that the second embodiment is the same as the first embodiment in that the side electrode 3b is used as the common electrode and the side electrode 3a is used as the individual electrode. Further, the second embodiment is the same as first embodiment in that the insulating film 6 is provided such that the short-circuit of the conducting adhesive material 8a for bonding the wiring members to the individual electrodes to the side electrode 3b is prevented.

Next, the third embodiment of the present invention will be explained. In the second embodiment, the example in which the notch is formed in the corner part of the multilayered structure to insulate the flat electrode 4a from the side electrode 3b and insulate the flat electrode 4b from the side electrode 3a has been shown, however, in the third embodiment, an example in which insulating films of an insulating resin is provided in the corner parts of the multilayered structure will be shown.

Figure 4:
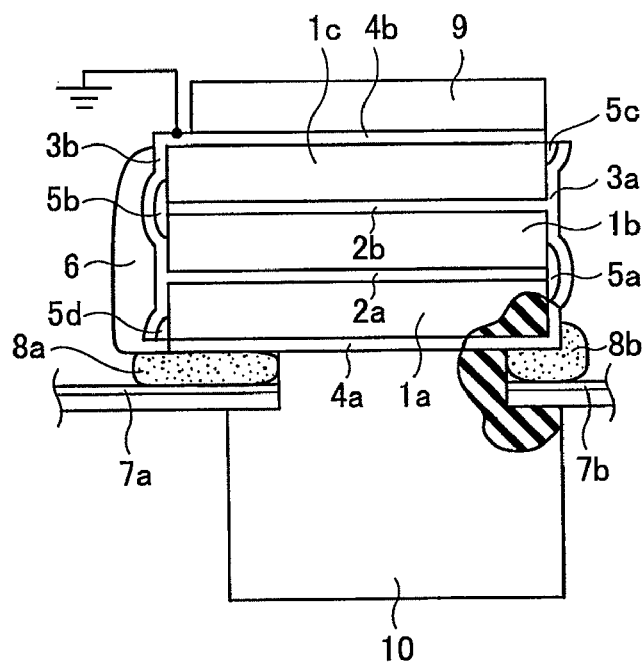
FIG. 4 is a front view showing an ultrasonic probe according to the third embodiment of the present invention.

FIG. 4 is a front view showing an ultrasonic probe according to the third embodiment of the present invention. As shown in FIG. 4, an insulating film 5c of an insulating resin is provided inside of the end part of the side electrode 3a at the flat electrode 4b, and an insulating film 5d of the insulating resin is provided inside of the end part of the side electrode 3b at the flat electrode 4a.

The insulating film 6 covers the corner part where the side electrode 3b and the flat electrode 4a are separated by the insulating film 5d. In the third embodiment, the end part of the side electrode 3b at the flat electrode 4a side is covered by the insulating film 6, and the short-circuit of the conducting adhesive material 8a to the side electrode 3b can be prevented.

Next, the fourth embodiment of the present invention will be explained. In the first to third embodiments, the example of multilayered structure of whole surface electrode structure has been shown, however, in the fourth embodiment, an example of multilayered structure of alternating electrode structure will be shown.

Figure 5:
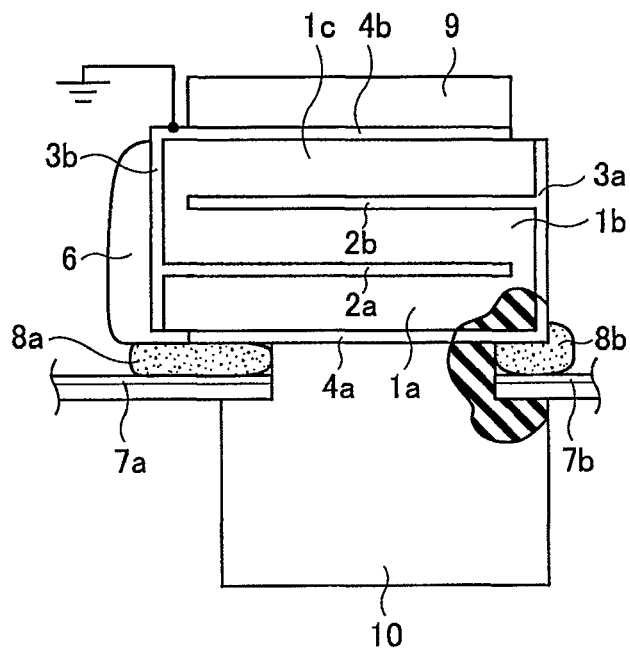
FIG. 5 is a front view showing an ultrasonic probe according to the fourth embodiment of the present invention.

FIG. 5 is a front view showing an ultrasonic probe according to the fourth embodiment of the present invention. As shown in FIG. 5, the internal electrode 2a does not reach the side surface of the side electrode 3a but ends within the piezoelectric material, and the internal electrode 2b does not reach the side surface of the side electrode 3b but ends within the piezoelectric material. Accordingly, the internal electrode 2a is insulated from the side electrode 3a, and the internal electrode 2b is insulated from the side electrode 3b. Further, the flat electrode 4a does not reach the side surface of the side electrode 3b like the internal electrode 2b, and the flat electrode 4b does not reach the side surface of the side electrode 3a like the internal electrode 2a. Thereby, the flat electrode 4a is insulated from the side electrode 3b, and the flat electrode 4b is insulated from the side electrode 3a.

The insulating film 6 covers nearly the entire exposed surface of the side electrode 3b and covers the corner part of the piezoelectric material layer 1a at the side electrode 3b side. In the case of the alternating electrode structure, the end part of the side electrode 3b at the flat electrode 4a side is covered by the insulating film 6 and the short-circuit of the conducting adhesive material 8a to the side electrode 3b can be prevented.

Next, the fifth embodiment of the present invention will be explained.

Figure 6:
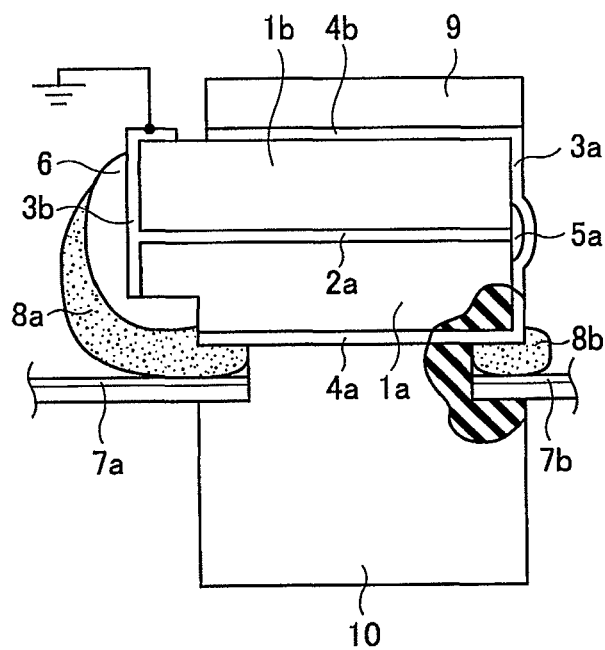
FIG. 6 is a front view showing an ultrasonic probe according to the fifth embodiment of the present invention.

FIG. 6 is a front view showing an ultrasonic probe according to the fifth embodiment of the present invention. As shown in FIG. 6, the conducting adhesive material 8a is formed to the upper part of the insulating film 6. The conducting adhesive material 8a flows out from the notch part (groove) and covers the greater part of the insulating film 6 at the flat electrode 4a side.

In this manner, the conducting adhesive material 8a not only covers the joint part of the end of the flat electrode 4a and the wiring member 7a but also widely covers the insulating film 6, and thus, the mechanical strength of the joint part and the side surface of the multilayered structure can be improved. Further, the electric disconnection can be prevented by sufficient filling of the conducting adhesive.

Next, the sixth embodiment of the present invention will be explained. The sixth embodiment is a modification of the first embodiment, however, the second or fifth embodiment may be modified in the same manner.

FIG. 7 shows an internal structure of an ultrasonic probe according to the sixth embodiment of the present invention. In FIG. 7, (a) is a front view, (b) is a left-side view, and (c) is a right-side view.

When the ultrasonic probe according to the first embodiment is manufactured, as shown in FIG. 2E, the insulating film 6 is formed by applying a highly insulating resin to the surface of the side electrode 3b and the part of the notch part (groove) including the end part of the side electrode 3b. At the step, in order to reliably cover the end part of the side electrode 3b exposed on the notch part, the amount of highly insulating resin should be made larger and the highly insulating resin may flow out from the notch part. If the highly insulating resin flows out from the notch part, the highly insulating resin spreads out on the flat electrode 4a and the physical connection and electric connection between the flat electrode 4a and the wiring member 7a (FIG. 2F) becomes defective. On this account, in the sixth embodiment, the notch part for dividing the side electrode 3b and the flat electrode 4a has a two-step configuration as shown in FIG. 7.

Next, a method of manufacturing the ultrasonic probe according to the sixth embodiment of the present invention will be explained. The process prior to the steps of applying a coating to the multilayered structure with electrode materials (conducting films) to be the side electrodes 3a and 3b and the flat electrodes 4a and 4b as shown in FIG. 2C and forming the groove on the flat electrode 4b such that the flat electrode 4b and the side electrode 3b are electrically divided as shown in FIG. 2D is the same as that in the first embodiment.

Figure 8A:
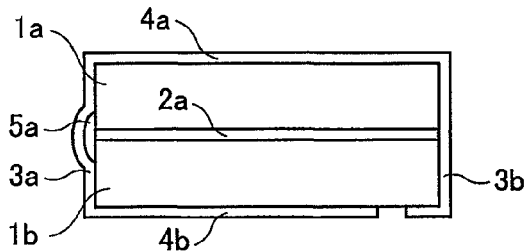
FIGS. 8A-8C are diagrams for explanation of the method of manufacturing the ultrasonic probe according to the sixth embodiment of the present invention.
Figure 8B:
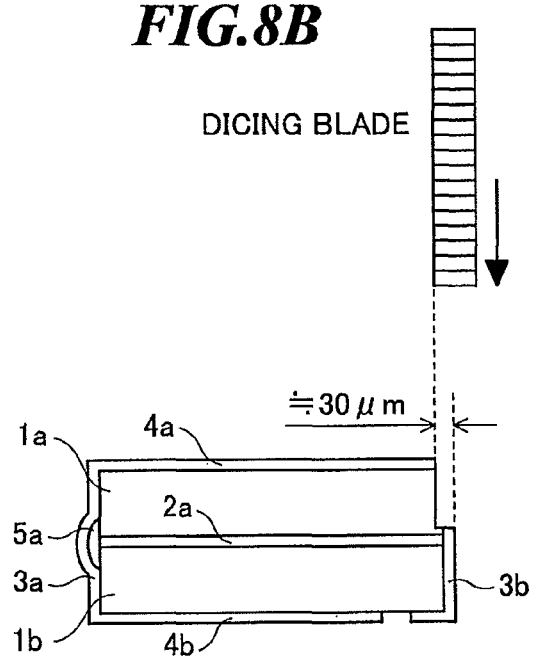
Figure 8C:
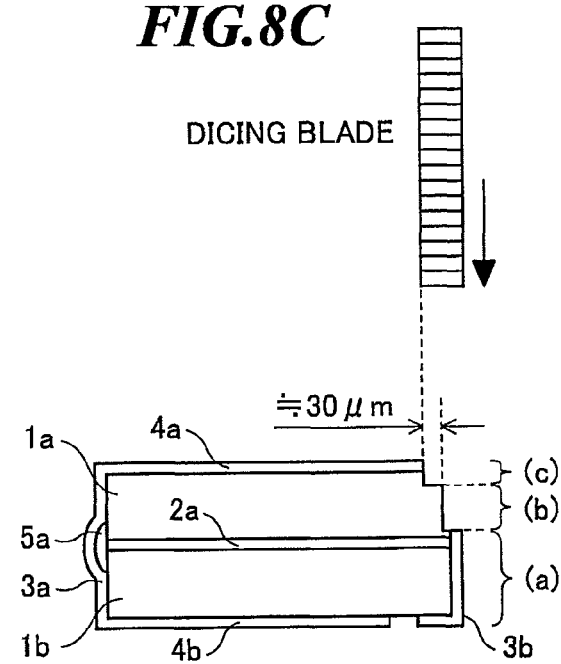

FIGS. 8A-8C are diagrams for explanation of the method of manufacturing the ultrasonic probe according to the sixth embodiment of the present invention. In the multilayered structure shown in FIG. 8A, in order to electrically divide the flat electrode 4b and the side electrode 3b, as shown in FIG. 8B, a groove is formed at a first depth from the surface including the flat electrode 4a and at a second depth (e.g., about 30 µm) from the surface including the side electrode 3b on the corner part of the multilayered structure (including a part of the piezoelectric material layer 1a) where the surface including the flat electrode 4a and the surface including the side electrode 3b intersect. In this example, using a dicing blade attached to a dicing saw or cutting saw and rotated, the corner part of the multilayered structure is cut off in the array arrangement direction.

Furthermore, as shown in FIG. 8C, a groove is formed at a third depth shallower than the first depth from the surface including the flat electrode 4a and at a fourth depth deeper than the second depth (e.g., about 60 µm=30 µm+30 µm) from the surface including the side electrode 3b. Thereby, the notch part having a two-step configuration is formed. In this example, using the dicing blade, the corner part of the multilayered structure is cut off in the array arrangement direction. By repeating the steps, a notch part having a multi-step configuration may be formed.

In the example shown in FIG. 8C, three regions (a) to (c) at different levels are formed on the side surface of the multilayered structure. When a highly insulating resin is applied to a part of the region (a) and the region (b), the surface tension is made stronger by the level difference between the region (b) and the region (c), and thereby, the highly insulating resin is prevented from spreading out to the region (c). In addition, the highly insulating resin can reliably cover the end part of the side electrode 3b exposed on the notch part, the yield of the ultrasonic probe can be improved.

The invention claimed is:

1. An ultrasonic probe including plural multilayered piezoelectric elements arranged in a row, each of said plural multilayered piezoelectric elements comprising:

a multilayered structure in which plural piezoelectric material layers and at least one internal electrode are alternately stacked;

a first flat electrode formed on a piezoelectric material layer located on one end of said multilayered structure;

a second flat electrode formed on a piezoelectric material layer located on the other end of said multilayered structure;

a first side electrode formed on a first side surface of said multilayered structure and connected to odd-numbered electrodes of said first and second flat electrodes and said at least one internal electrode, said odd-numbered electrodes including said first flat electrode;

a second side electrode formed on a second side surface of said multilayered structure and connected to even-numbered electrodes of said first and second flat electrodes and said at least one internal electrode;

an insulating film formed at a second side surface side of said multilayered structure;

a wiring member bonded to said first flat electrode on said one end of said multilayered structure by using a conducting adhesive material;

wherein said wiring member is provided at the second side surface side of said multilayered structure in a first multilayered piezoelectric element of said plural multilayered piezoelectric elements, said wiring member is provided at a first side surface side of said multilayered structure in a second multilayered piezoelectric element adjacent to said first multilayered piezoelectric element of said plural multilayered piezoelectric elements, and said insulating film electrically separates said second side electrode and said conducting adhesive material in said first multilayered piezoelectric element.

2. The ultrasonic probe according to claim 1, wherein a first groove is formed in a corner part of said multilayered structure where a surface including said first flat electrode and a surface including said second side electrode intersect, and a second groove is formed in parallel with said first groove in said second flat electrode, and thereby, (i) an individual electrode including said first flat electrode, said first side electrode, and a part of said second flat electrode and (ii) a common electrode including said second side electrode and a part of said second flat electrode are formed.

3. The ultrasonic probe according to claim 2, wherein said first groove is formed by forming a groove at a first depth from the surface including said first flat electrode and at a second depth from the surface including said second side electrode, and further forming a groove at a third depth shallower than the first depth from the surface including said first flat electrode and at a fourth depth deeper than the second depth from the surface including said second side electrode in the corner part of said multilayered structure where the surface including said first flat electrode and the surface including said second side electrode intersect.

4. The ultrasonic probe according to claim 1, wherein said conducting adhesive material is formed to cover a part of said insulating film.

5. The ultrasonic probe according to claim 1, wherein said insulating film includes a resin.

6. The ultrasonic probe according to claim 1, wherein each of said plural piezoelectric material layers has a thickness not larger than 130 µm.

* * * * *